(12) United States Patent
    Gandras

(10) Patent No.: US 12,629,497 B2
(45) Date of Patent: May 19, 2026

(54) INTRAVASCULAR SAFETY GUIDEWIRE

(71) Applicant: Eric J. Gandras, Great Neck, NY (US)

(72) Inventor: Eric J. Gandras, Great Neck, NY (US)

( * ) Notice: Subject to any disclaimer, the term of this patent is extended or adjusted under 35 U.S.C. 154(b) by 264 days.

(21) Appl. No.: 18/407,523

(22) Filed: Jan. 9, 2024

(65) Prior Publication Data

US 2024/0245888 A1     Jul. 25, 2024

Related U.S. Application Data

(60) Provisional application No. 63/440,706, filed on Jan. 24, 2023.

(51) Int. Cl.
    *A61M 25/01*      (2006.01)
    *A61M 25/02*      (2006.01)
    *A61M 25/09*      (2006.01)
    *A61M 29/00*      (2006.01)
    *A61M 29/02*      (2006.01)

(52) U.S. Cl.
    CPC .... *A61M 25/0169* (2013.01); *A61M 25/0172* (2013.01); *A61M 25/02* (2013.01); *A61M 25/09* (2013.01); *A61M 29/00* (2013.01); *A61M 2025/09058* (2013.01); *A61M 2025/09141* (2013.01); *A61M 2029/025* (2013.01); *A61M 2205/0266* (2013.01)

(58) Field of Classification Search
    CPC .......... A61M 25/0169; A61M 25/0172; A61M 25/09; A61M 25/09041; A61M 2025/09116; A61M 2025/09125
    USPC ....................................................... 600/585
    See application file for complete search history.

(56) References Cited

U.S. PATENT DOCUMENTS

| | | | | |
|---|---|---|---|---|
| 5,919,161 A * | 7/1999 | Hill, III | .......... | A61M 25/09041 604/95.01 |
| 9,108,027 B2 * | 8/2015 | Eubanks | ................ | A61M 25/09 |
| 9,504,806 B2 * | 11/2016 | Gallacher | ............. | A61M 25/09 |
| 9,775,782 B2 * | 10/2017 | Delegge | ............... | A61J 15/0015 |
| 11,819,641 B2 * | 11/2023 | Dacanay | .......... | A61M 25/09041 |
| 2009/0093670 A1 * | 4/2009 | Annest | ................... | A61M 25/09 606/139 |
| 2018/0304049 A1 * | 10/2018 | Bennett | ................. | A61M 25/02 |
| 2019/0262587 A1 * | 8/2019 | Gottlieb | ................ | A61M 25/09 |
| 2020/0086092 A1 * | 3/2020 | Waldron | ......... | A61M 25/09041 |
| 2020/0360669 A1 * | 11/2020 | Dacanay | ......... | A61M 25/09041 |
| 2021/0016059 A1 * | 1/2021 | Brown | ............. | A61M 25/0606 |

(Continued)

*Primary Examiner* — Adam J Eiseman
(74) *Attorney, Agent, or Firm* — Bruce A. Lev

(57) ABSTRACT

An intravascular safety guidewire including an elongated main shaft, a distal terminus extending from the elongated main shaft, and an anchor rotatably connected to the distal terminus. In use, a needle is inserted into a patient's vein, then the intravascular safety guidewire is placed through the needle and into the vein, the needle is then removed over the intravascular safety guidewire, then a venous catheter is exchanged over the intravascular safety guidewire following serial dilatation using the Seldinger technique. Tubes such as dilators and catheters can then be placed over the intravascular safety guidewire and the intravascular safety guidewire ultimately removed. Currently complications can arise if a guidewire becomes retained inside a patient during an endovascular procedure, which is associated with high morbidity and mortality rates. The instant intravascular safety guidewire with its rotatable anchor reduces the likelihood of this complication.

2 Claims, 9 Drawing Sheets

(56)     References Cited

U.S. PATENT DOCUMENTS

2023/0398332 A1 *  12/2023  Hindmarsh  .....  A61M 25/09041
2025/0213825 A1 *   7/2025  Carpenter  .......  A61M 25/09041

* cited by examiner

INTRAVASCULAR SAFETY GUIDEWIRE

CROSS-REFERENCE TO RELATED APPLICATION

The present application is related to and claims priority from prior provisional application Ser. No. 63/440,706, filed Jan. 24, 2023 which is incorporated herein by reference.

COPYRIGHT NOTICE

BACKGROUND OF THE INVENTION

1. Field of the Invention

This invention relates generally to interventional medical guidewires, and more specifically to intravascular safety guidewires.

2. Description of the Related Art

Interventional guidewires are used for medical endovascular surgical interventions in both arteries and veins. They are generally safe but they can be associated with complications. For example, retained guidewires during central venous line insertion is a preventable error that is considered a "never event" by the Joint Commission, which means it should never occur. However, the incidence is 1:3291 procedures. With more than 5 million central venous catheters placed in the United States annually this error occurs in over 1500 patients/year. The reported mortality is up to 20%, with complications including arrhythmias, thrombosis and cardiac perforation and tamponade. Interventional Radiologists are in the unique position of both performing image-guided venous access procedures as well as retrieving retained guidewires once they are recognized. The occurrence of this error has been attributed to fatigue, distraction, inexperience and a high workload. None of the prior art apparatuses or systems addresses this significant pervasive problem nor have been developed to reduce this error. Thus, a need exists for an intravascular safety guidewire to avoid the above-mentioned problems.

BRIEF SUMMARY OF THE INVENTION

In view of the foregoing disadvantages inherent in the known types of intravascular guidewires or the like in the prior art, the present invention provides a novel intravascular safety guidewire. As such, the general purpose of the present invention, which will be described subsequently in greater detail, is to provide an intravascular safety guidewire including an elongated main shaft, a distal terminus extending from the main shaft, and an anchor rotatably connected to the distal terminus, with all the advantages of the prior art and none of the disadvantages.

There has thus been outlined, rather broadly, the more important features of the invention in order that the detailed description thereof that follows may be better understood and in order that the present contribution to the art may be better appreciated.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. The invention is capable of other embodiments and of being practiced and carried out in various ways. Also, it is to be understood that the phraseology and terminology employed herein are for the purpose of descriptions and should not be regarded as limiting.

BRIEF DESCRIPTION OF THE DRAWINGS

The figures which accompany the written portion of this specification illustrate embodiments according to the teachings of the present invention.

The various embodiments of the present invention will hereinafter be described in conjunction with the appended drawings.

DETAILED DESCRIPTION

The concept of the intravascular safety guidewire is simple, a guidewire whose default configuration passively contains an "anchor" in the form of a rotating small fragment of guidewire that has to be actively placed into a neutral position in order to feed devices over it in order to perform placement using a Seldinger technique. Because distractions are a major contributor to errors, this configuration would force the operator to pay attention and focus on the guidewire actively with each exchange of a device tracking over the guidewire during endovascular procedures. Also, if the guidewire were to inadvertently become advanced towards the vascular system the "anchor" (if not confined in a catheter or dilator) would prevent entry and thus avoid the error. The anchor will prevent embolization of the guidewire into the circulation below the skin surface.

Figure 1:
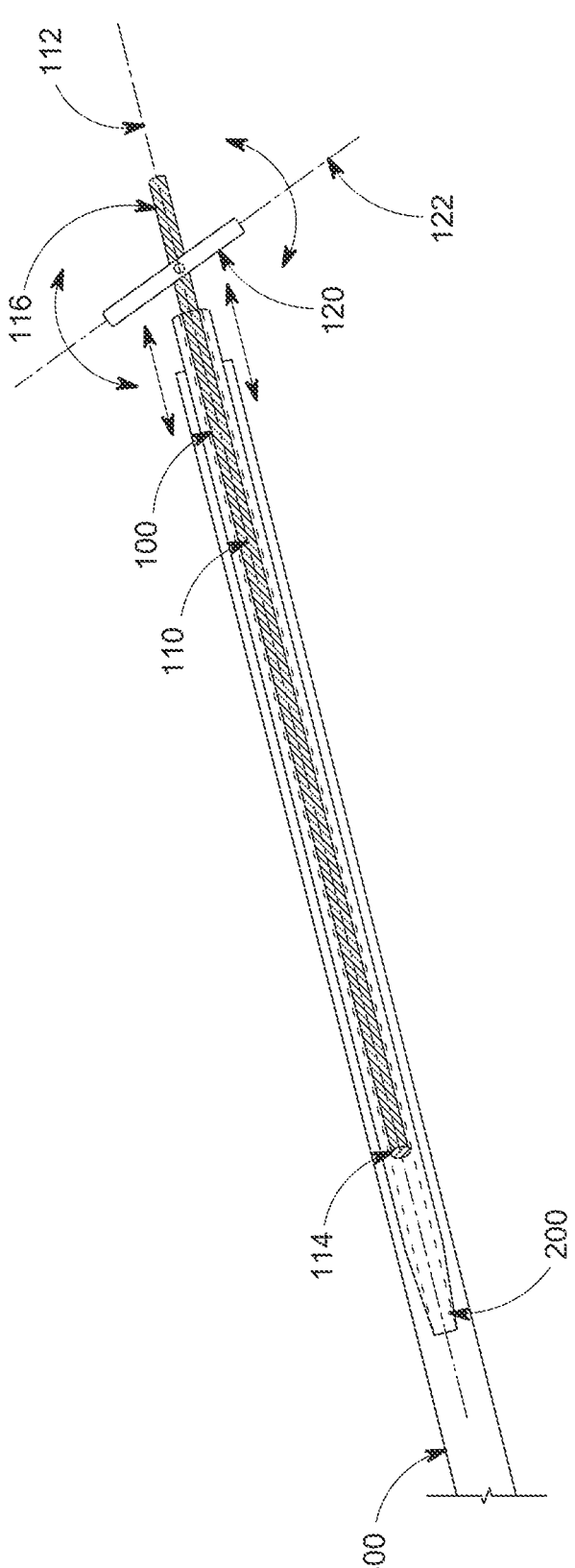
FIG. 1 shows a view of the intravascular safety guidewire being inserted through a hollow needle and into a blood vessel of a patient according to an embodiment of the present invention.

Referring now to FIG. 1, the intravascular safety guidewire 100 includes an elongated main shaft 110 including a distal terminus 116 and an anchor 120 rotatably connected to the distal terminus 116. The elongated main shaft 110 may consists of stainless steel, nitinol, or any other materials used in the prior art. Its diameter range may be between 0.035 and 0.038 inches. The distal terminus 116 may taper to a diameter range of between 0.010 and 0.018 inches, and its length in a range between 1.0 and 10 mm longer than 0.5 times the length of the rotating anchor 120 in order to allow free movement and rotation with respect to the elongated main shaft 110 and distal terminus 116. The tip of the distal terminus 116 may be shaped to a 90 degree angle to provide a pivot point for pivot receiver 124 of the rotating anchor 120 to attach to, or include a pivot post 118 at a middle section thereof adapted to be placed within pivot receiver 124 of the rotating anchor 120 to allow rotation therebetween. The rotating anchor 120 may have a diameter range between 0.010 and 0.018 inches and a length that can be in a range between 1.0 and 10.0 cm. The rotating anchor 120 along with the distal terminus 116 combined diameters should not exceed the diameter of the main shaft 110.

Figure 7:
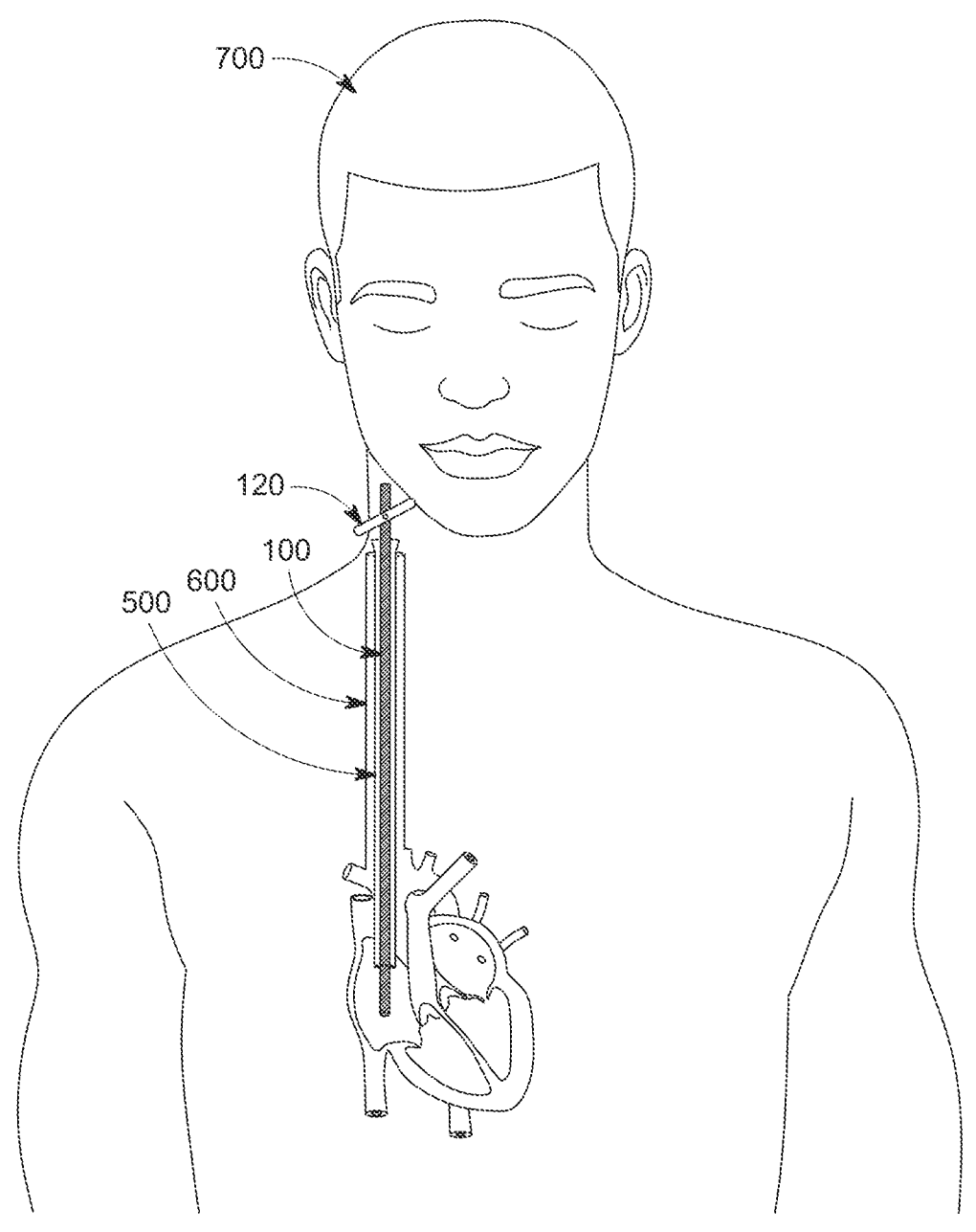
FIG. 7 shows a catheter placed within a blood vessel of the heart of a patient using the intravascular safety guidewire according to the preferred embodiment of the present invention of FIG. 1.

As shown in FIG. 7, the intravascular safety guidewire 100 is inserted into a blood vessel 600 of a patient 700, in this case the right internal jugular vein as an example of use during placement of a central venous catheter 500, through their Superior Vena Cava, and into the patient's heart.

In use in a known venous access procedure, for example, a catheter 500 (a central venous catheter or "central line") is inserted using the "Seldinger" technique which entails placing a needle into a vein, then placing the guide wire into the vein a sufficient amount to secure access, then exchanging the needle over the guide wire following serial dilatation for the catheter. One has to place the tubes over the wire and the wire is ultimately removed at the end of the procedure. When the catheter or dilator is placed over the wire there has to be a portion of the wire exposed and available distally to the device that one can grab to "pin" and give tension to allow sufficient countertension to "track" the catheter over it.

Wires can be lost when one is not careful to focus on the back of the wire and allows it get too close to the skin or it stays in the device and gets pushed in, which the anchor may not be able to prevent. The idea is to have to actively straighten the wire to zero degrees or neutral to pass items over it, but the default is angulated so that it can catch and anchor the wire if it migrates to the skin.

When tracking dilators or catheters over the wire one has to place the wire into neutral. There can be friction between devices and wires. As such some catheters are hydrophilic and coated with a PTFE coating among other substances. Guide wires are typically stainless steel and include an outer wire wound around an inner core wire so if they break they will not fragment and fall off inside a patient's vascular system. Nitinol or other alloys are used in the prior art and the safety guidewire could be embodied by any of these materials.

As shown in FIGS. 1-7, the instant invention is used within an endovascular surgical intervention, wherein a catheter 500 is adapted to be inserted into a blood vessel 600 of a patient 700 using a hollow needle 200, a guide wire, and a series of dilators 300. The improvement comprises an intravascular safety guidewire 100 replacing the guide wire, wherein the intravascular safety guidewire 100 comprises an elongated main shaft 110 including an elongated axis 112 along the its length, a proximal end 114 adapted to be inserted through the hollow needle, and a distal terminus 116 located on the opposite end of the elongated main body opposite the proximal end, and including a pivot post 118 extending from the elongated axis; and a rotating anchor 120 including an elongated body including an elongated axis 122 along the length of the elongated body, and a pivot receiver 124 located at a center portion of its elongated body and adapted to receive the pivot post 118 of the elongated main shaft 110 therein, such that the rotating anchor 120 is adapted to rotate with respect to the elongated main shaft 110.

Figure 2:
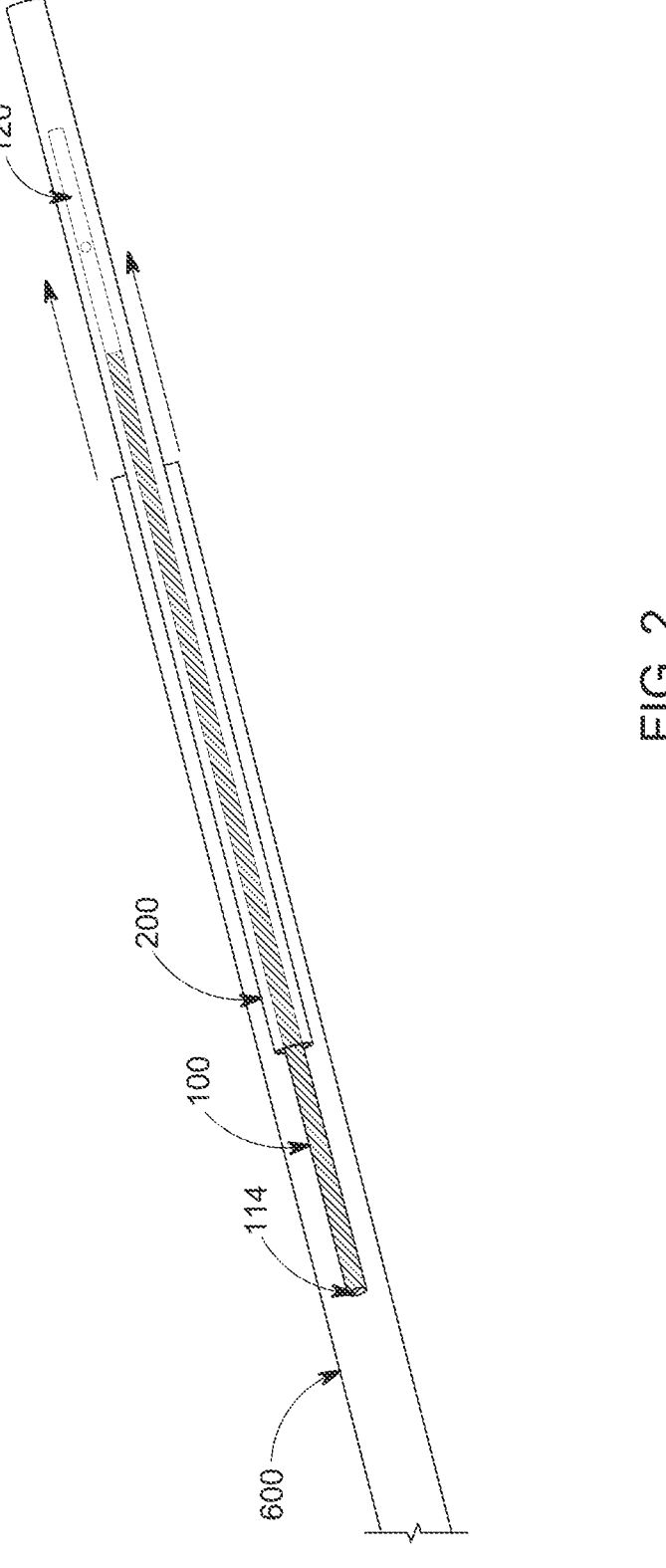
FIG. 2 shows a view of the hollow needle being removed over the intravascular safety guidewire and out of the blood vessel of the patient according to an embodiment of the present invention of FIG. 1.
Figure 3:
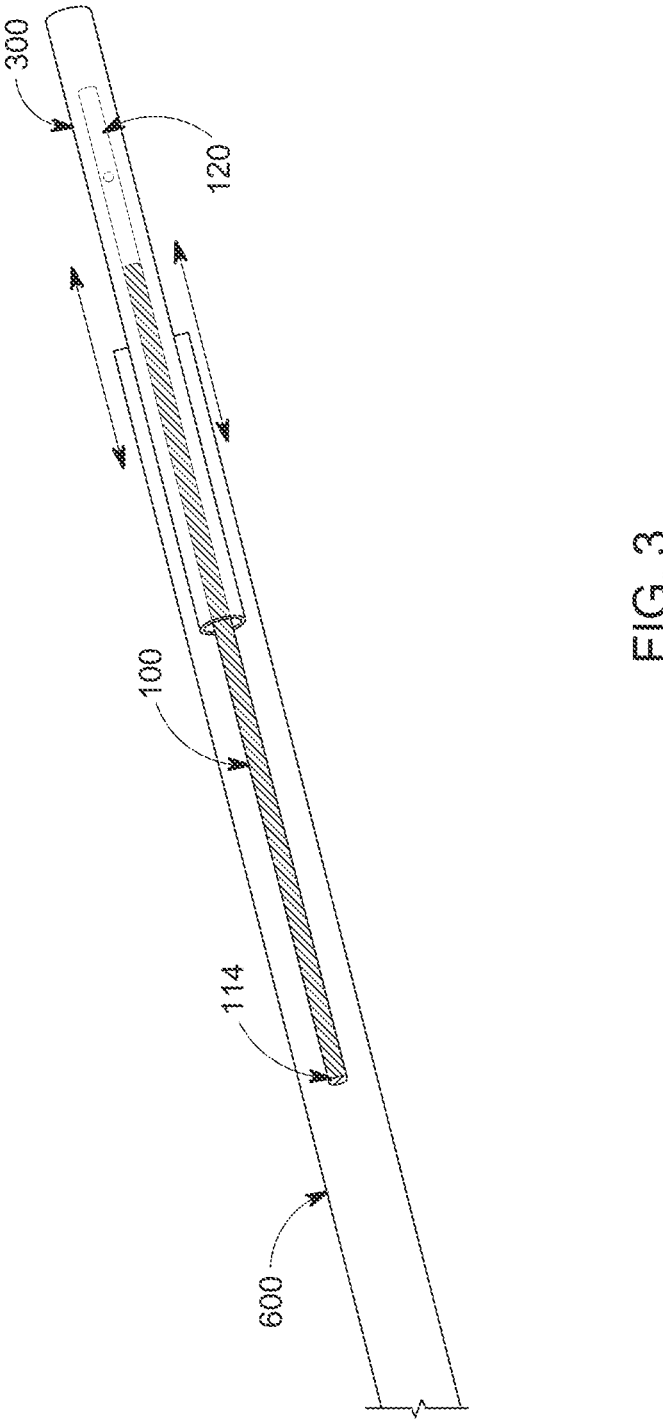
FIG. 3 shows a dilator being slid onto the intravascular safety guidewire and into the blood vessel of the patient according to the preferred embodiment of the present invention of FIG. 1.
Figure 4:
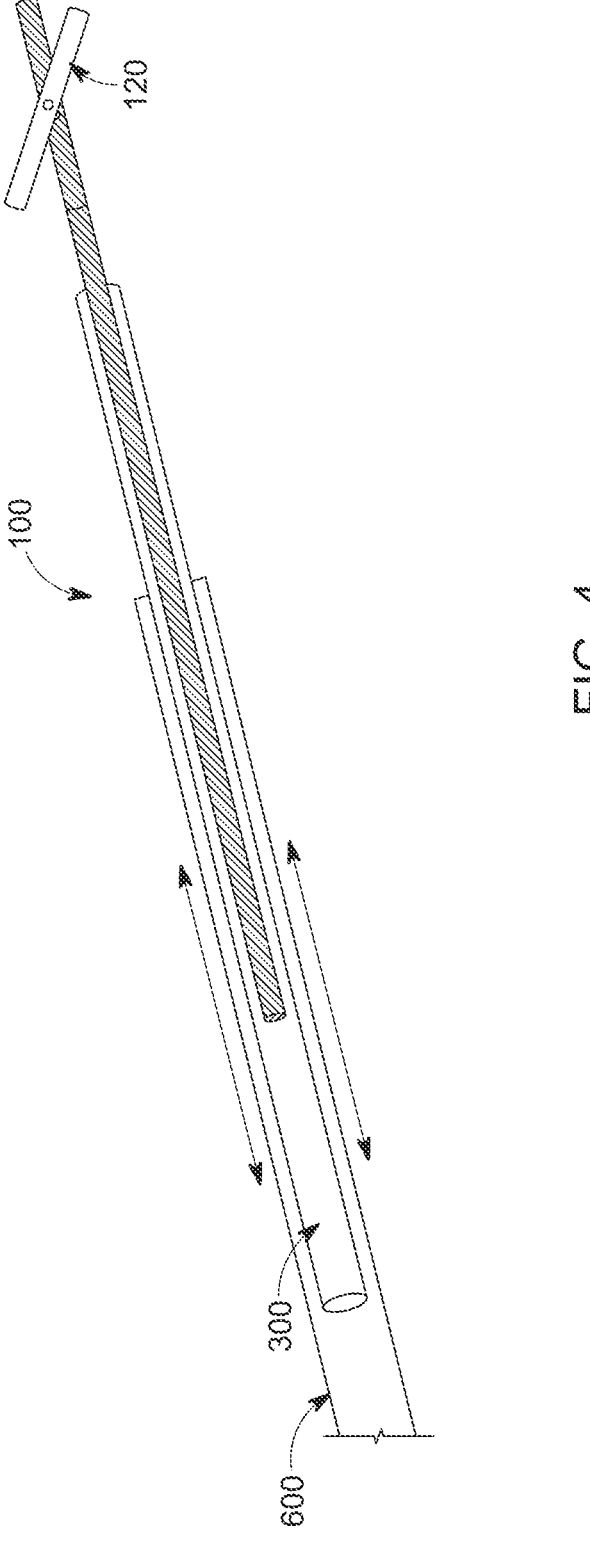
FIG. 4 shows the dilator being pushed into the blood vessel of the patient according to the preferred embodiment of the present invention of FIG. 1.
Figure 5:
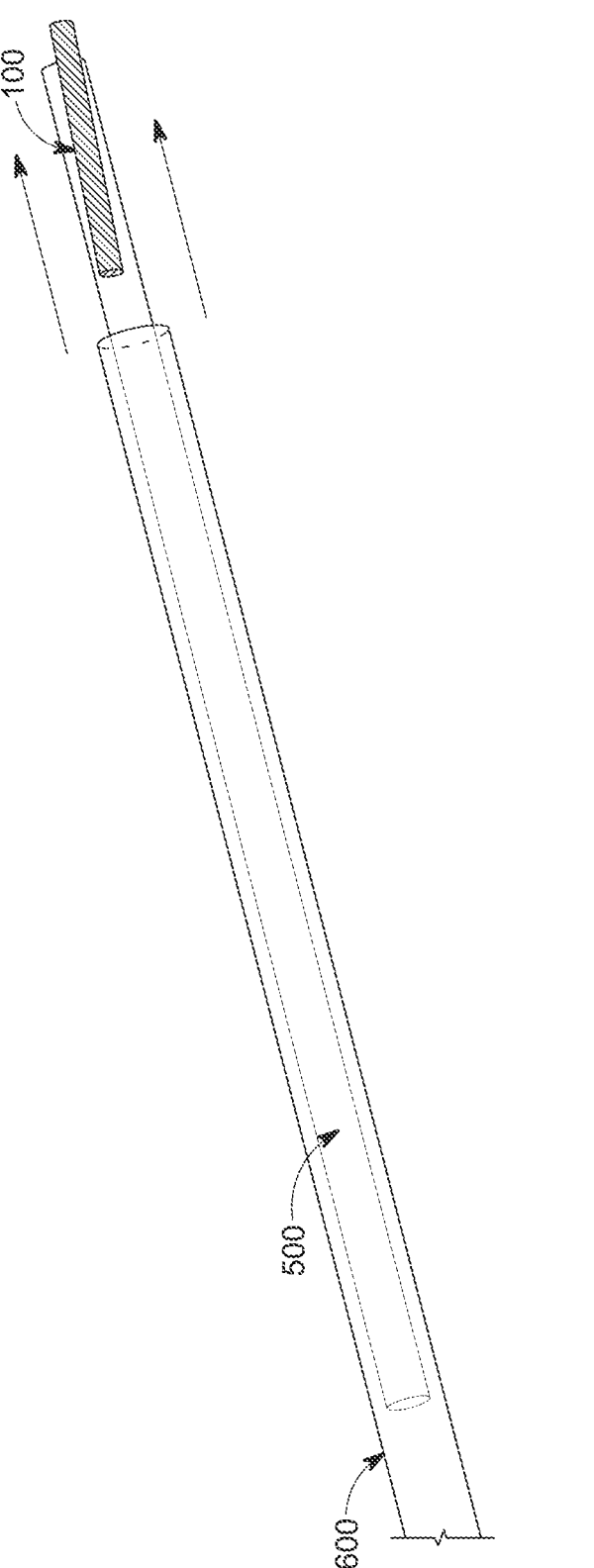
FIG. 5 shows a catheter placed within the blood vessel of the patient and the intravascular safety guidewire being removed according to the preferred embodiment of the present invention of FIG. 1.
Figure 6:
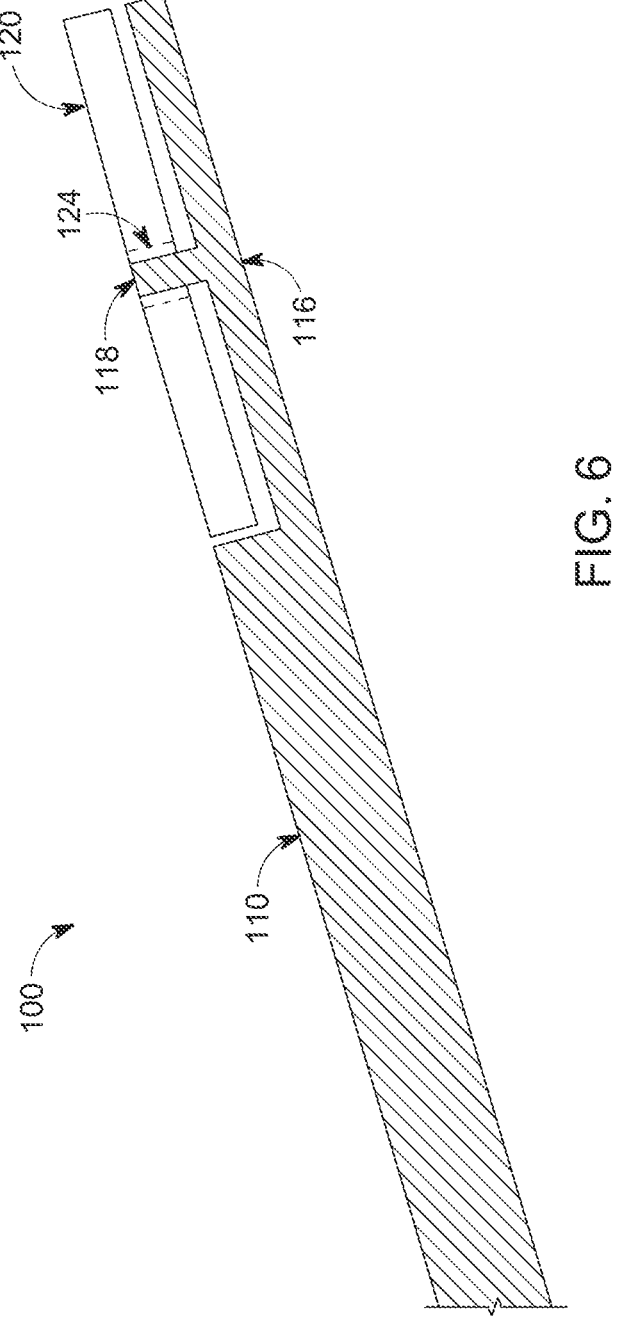
FIG. 6 shows a cross section of the intravascular safety guidewire according to the preferred embodiment of the present invention of FIG. 1.

When in use, the hollow needle 200 is inserted into a blood vessel 600 of a patient 700, then the rotating anchor 120 of the intravascular safety guidewire 100 is rotated such that its elongated axis 122 is in a non-parallel position, as shown in FIGS. 1, 4, and 7, to the elongated axis 112 of the elongated main shaft 110, thereby preventing the intravascular safety guidewire from slipping completely into the blood vessel of the patient; then the intravascular safety guidewire 100 is slid into and through the hollow needle 200 and into the blood vessel 600 of the patient until in a desired position; then the rotating anchor 120 of the intravascular safety guidewire is rotated such that its elongated axis 122 is in a parallel position, as shown in FIGS. 2 and 3, to the elongated axis 112 of the elongated main shaft 110, thereby allowing the hollow needle to be slid over the intravascular safety guidewire and the rotating anchor and off the intravascular safety guidewire completely; then a first dilator 300 is slid over the rotating anchor 120, as shown in FIG. 3, while in the parallel position and onto the intravascular safety guidewire 100; then once the dilator 300 has passed beyond the rotating anchor 120 the rotating anchor of the intravascular safety guidewire is again rotated such that its elongated axis 122 is in a non-parallel position, as shown in FIG. 4, to the elongated axis 112 of the elongated main shaft 110, thereby again preventing the intravascular safety guidewire 100 from slipping completely into the blood vessel 600 of the patient; then the first dilator 300 is pushed into the blood vessel 600 of the patient until in a desired position; then the process is repeated for successively larger diameter dilators 300 until the desired diameter catheter 500 is placed upon the intravascular safety guidewire 100 and pushed within said blood vessel 600 until in a desired position; then the intravascular safety guidewire 100 is slid out from the catheter 500 and the blood vessel 600 of the patient, as shown in FIG. 5, leaving the catheter 500 therein.

Figure 8:
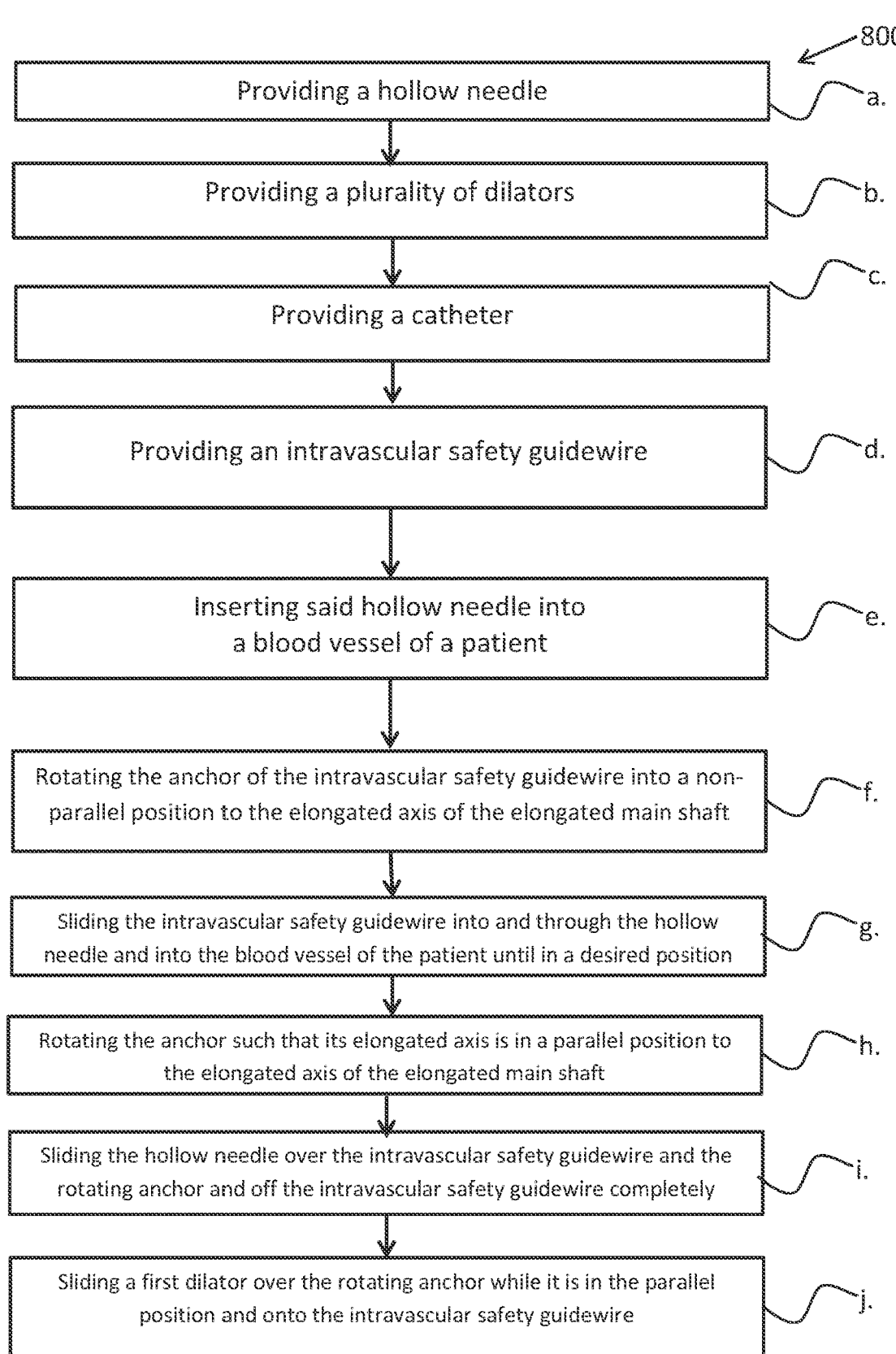
FIG. 8 shows a flow chart of method steps (a) through (j) according to the preferred embodiment of the present invention of FIG. 1.
Figure 9:
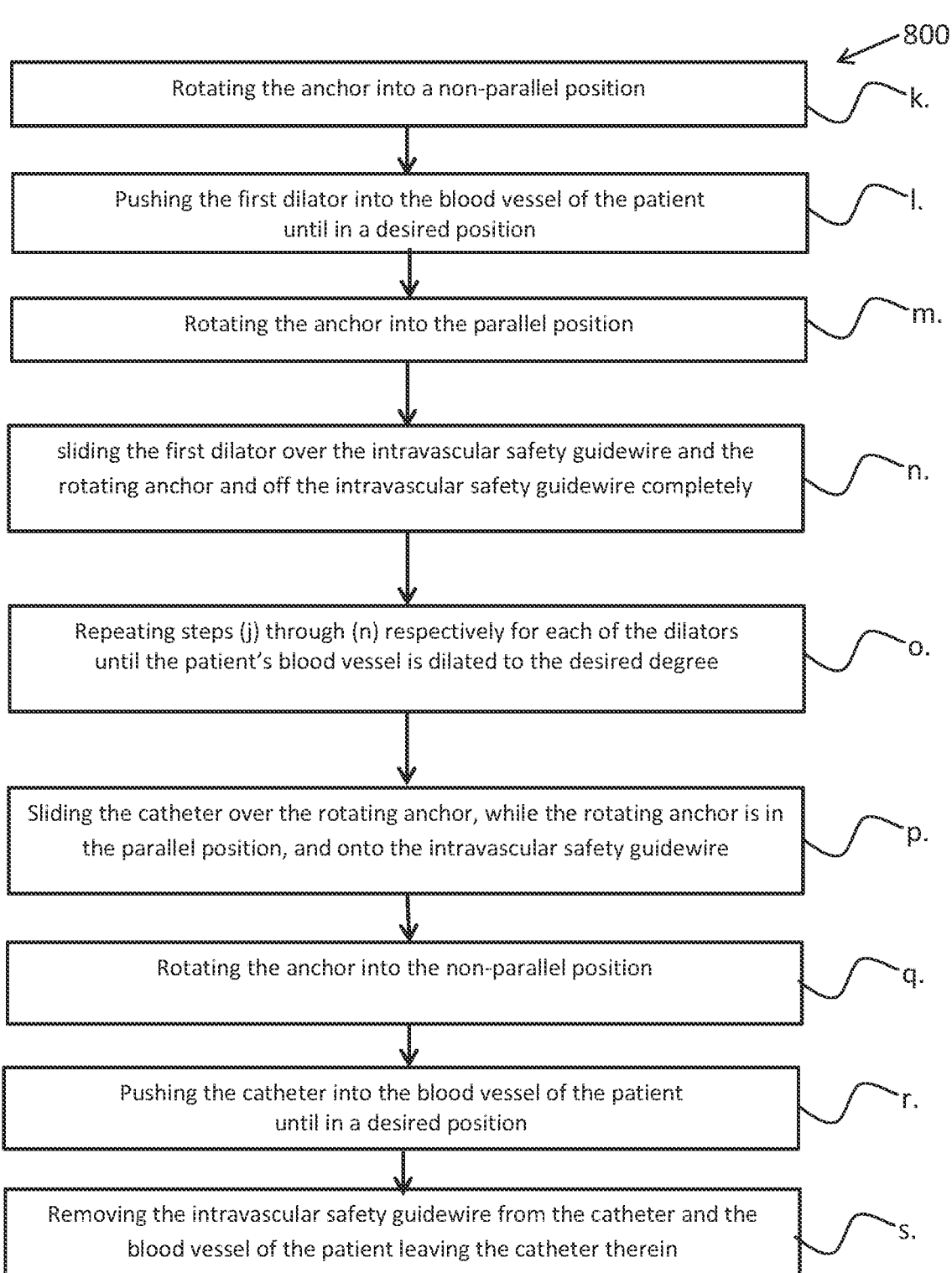
FIG. 9 shows a flow chart of method steps (k) through (s) according to the preferred embodiment of the present invention of FIG. 1.

As shown in FIGS. 8 through 9, the method 800 of placing a catheter into a blood vessel, comprises the steps of (a) providing a hollow needle 200; (b) providing a plurality of dilators 300 having successively larger diameters from one another; (c) providing a catheter 500; (d) providing an intravascular safety guidewire 100 as set forth previously: (e) inserting the hollow needle 200 into a blood vessel of a patient; (f) rotating the anchor 120 of the intravascular safety guidewire such that its elongated axis is in a non-parallel position to the elongated axis of the elongated main shaft, thereby preventing the intravascular safety guidewire from slipping completely into the blood vessel of the patient; (g) sliding the intravascular safety guidewire 100 into and through the hollow needle 200 and into the blood vessel of the patient until in a desired position; (h) rotating the anchor 120 of the intravascular safety guidewire such that its elongated axis is in a parallel position to the elongated axis of the elongated main shaft; (i) sliding the hollow needle 200 over the intravascular safety guidewire and the rotating anchor and off the intravascular safety guidewire completely; (j) sliding a first dilator 300 over the rotating anchor 120 while it is in the parallel position with respect to the main shaft of the intravascular safety guidewire and onto the intravascular safety guidewire 100; (k) rotating the anchor 120 of the intravascular safety guidewire once the first dilator has passed over and beyond the rotating anchor such that its elongated axis is in the non-parallel position to the elongated axis of the elongated main shaft, thereby again preventing the intravascular safety guidewire from slipping completely into the blood vessel of the patient; (l) pushing the first dilator 300 into the blood vessel 600 of the patient until in a desired position; (m) rotating the anchor 120 of the intravascular safety guidewire such that its elongated axis is in the parallel position to the elongated axis of the elongated main shaft; (n) sliding the first dilator 300 over the intravascular safety guidewire and the rotating anchor and off the intravascular safety guidewire completely; (o) repeating steps (j) through (n) respectively for each of the dilators 300 until the blood vessel 600 is dilated to the desired degree; (p) sliding the catheter 500 over the rotating anchor 120, while the rotating anchor is in the parallel position, and onto the intravascular safety guidewire; (q) rotating the anchor 120 of the intravascular safety guidewire such that its elongated axis is in the non-parallel position to the elongated axis of the elongated main shaft, thereby again preventing the intravascular safety guidewire from slipping completely into the blood vessel of the patient; (r) pushing the catheter 500 into the blood vessel 600 of the patient until in a desired position; and (s) removing the intravascular safety guidewire 100 from the catheter and the blood vessel of the patient leaving the catheter therein.

It should further be noted that when the intravascular safety guidewire 100 has no device over it and is bare prior to advancing something over it, such as the dilator or catheter, the rotating anchor should be in a non-parallel configuration with the elongated main body, which will further limit the wire from entering a blood vessel. This is key when comparing to prior art devices which need to be over the guidewire to "lock" it in place as opposed to an intrinsic property of the wire itself which will be a stand-alone device without needing to add any adjunctive devices onto the dilators or catheter. Some of the prior art wires are lost when no one is paying attention.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention.

What is claimed is:

1. A surgical system wherein a catheter is adapted to be inserted into a blood vessel of a patient using a hollow needle, a guide wire, and a series of dilators, wherein the improvement comprises an intravascular safety guidewire replacing said guide wire, wherein said intravascular safety guidewire comprises:

an elongated main shaft including:
an elongated axis along the length of said elongated main shaft;
a proximal end adapted to be inserted through said hollow needle; and
a distal terminus located on the opposite end of said elongated main body opposite said proximal end, and including:
a pivot post extending from said elongated axis; and
a rotating anchor including:
an elongated body including:
an elongated axis along the length of said elongated body; and
a pivot receiver;
wherein said pivot receiver is located at a center portion of said elongated body and adapted to receive said pivot post therein, such that said rotating anchor is adapted to rotate with respect to said elongated main shaft;
wherein when in use, said hollow needle is inserted into a blood vessel of a patient; then said rotating anchor of said intravascular safety guidewire is rotated such that its elongated axis is in a non-parallel position to said elongated axis of said elongated main shaft, thereby preventing said intravascular safety guidewire from slipping completely into the blood vessel of said patient; then said intravascular safety guidewire is slid into and through said hollow needle and into said blood vessel of said patient until in a desired position; then said rotating anchor of said intravascular safety guidewire is rotated such that its elongated axis is in a parallel position to said elongated axis of said elongated main shaft, thereby allowing said hollow needle to be slid over said intravascular safety guidewire and said rotating anchor and off said intravascular safety guidewire completely; then a first dilator is slid over said rotating anchor while in said parallel position and onto said intravascular safety guidewire; then once said dilator has passed beyond said rotating anchor said rotating anchor of said intravascular safety guidewire is again rotated such that its elongated axis is in a non-parallel position to said elongated axis of said elongated main shaft, thereby again preventing said intravascular safety guidewire from slipping completely into the blood vessel of said patient; then said first dilator is pushed into said blood vessel of said patient until in a desired position; then the process is repeated for successively larger diameter dilators until the desired diameter catheter is placed upon said intravascular safety guidewire and pushed within said blood vessel until in a desired position; then said intravascular safety guidewire is slid out from said catheter and said blood vessel of said patient leaving the catheter therein.

2. The intravascular safety guidewire of claim 1, wherein said intravascular safety guidewire is formed from a material chosen from a list of materials consisting of stainless steel, and nitinol.

* * * * *